(12) United States Patent
Vikharankar et al.

(10) Patent No.: US 10,660,665 B2
(45) Date of Patent: May 26, 2020

(54) SURGICAL INSTRUMENTS FOR TISSUE REMOVAL

(71) Applicant: COVIDIEN LP, Mansfield, MA (US)

(72) Inventors: Yogesh K. Vikharankar, Maharashtra (IN); Jeevan Maddur Shankarsetty, Karnataka (IN)

(73) Assignee: Covidien LP, Mansfield, MA (US)

( * ) Notice: Subject to any disclaimer, the term of this patent is extended or adjusted under 35 U.S.C. 154(b) by 319 days.

(21) Appl. No.: 15/645,429

(22) Filed: Jul. 10, 2017

(65) Prior Publication Data
US 2019/0008540 A1   Jan. 10, 2019

(51) Int. Cl.
*A61B 17/32* (2006.01)
*A61B 17/3205* (2006.01)
*A61B 17/42* (2006.01)
*A61B 17/221* (2006.01)

(52) U.S. Cl.
CPC .. *A61B 17/3205* (2013.01); *A61B 17/320016* (2013.01); *A61B 17/42* (2013.01); *A61B 2017/2215* (2013.01); *A61B 2017/320024* (2013.01); *A61B 2017/4216* (2013.01); *A61B 2017/4233* (2013.01)

(58) Field of Classification Search
CPC ........ A61B 17/3205; A61B 17/320016; A61B 2017/320024; A61B 2017/4216; A61B 2017/4233; A61B 2017/2215; A61B 17/42; A61B 17/22031; A61B 17/221; A61F 2/01; A61F 2002/015; A61F 2002/016
See application file for complete search history.

(56) References Cited

U.S. PATENT DOCUMENTS

| | | | |
|---|---|---|---|
| 5,520,634 | A | 5/1996 | Fox et al. |
| 6,039,748 | A | 3/2000 | Savage et al. |
| 6,165,188 | A | 12/2000 | Saadat et al. |
| 6,468,228 | B1 | 10/2002 | Topel et al. |
| 6,821,285 | B2 | 11/2004 | Laufer et al. |
| 7,033,357 | B2 | 4/2006 | Baxter et al. |
| 7,918,795 | B2 | 4/2011 | Grossman |
| 8,308,746 | B2 | 11/2012 | Pravong et al. |

(Continued)

FOREIGN PATENT DOCUMENTS

WO   2009/039506 A1   3/2009

*Primary Examiner* — Tan-Uyen T Ho
*Assistant Examiner* — Erich G Herbermann
(74) *Attorney, Agent, or Firm* — Carter, DeLuca & Farrell LLP

(57) ABSTRACT

A surgical instrument for cutting tissue includes a sleeve, a shaft slidably disposed within the sleeve and defining a longitudinal axis, and a plurality of legs coupled to the shaft and disposed about the longitudinal axis. Each leg has a blade attached to an end portion thereof and each blade defines a cutting edge. The shaft is slidable relative to the sleeve between a collapsed configuration, wherein the legs are disposed within the sleeve, and an expanded configuration, wherein the legs extend distally and radially outwardly from the sleeve. In the expanded configuration, the cutting edge of each blade is disposed in a proximally-facing orientation. Alternatively, the shaft is rotatable relative to the sleeve to rotate the legs about the longitudinal axis, thereby rotating each blade through a circular cutting path defining a different diameter. Methods of cutting tissue are also provided.

6 Claims, 5 Drawing Sheets

(56) References Cited

U.S. PATENT DOCUMENTS

| | | |
|---|---|---|
| 9,668,763 B2 | 6/2017 | Sartor et al. |
| 2007/0225745 A1 | 9/2007 | Arnal et al. |
| 2008/0039883 A1 | 2/2008 | Nohilly |
| 2008/0097190 A1* | 4/2008 | Hornscheidt .... A61B 17/06066 600/421 |
| 2008/0269772 A1 | 10/2008 | Choi |
| 2011/0093009 A1* | 4/2011 | Fox .................... A61B 17/0057 606/216 |
| 2011/0121049 A1 | 5/2011 | Malinouskas et al. |
| 2012/0316572 A1 | 12/2012 | Rosenblatt et al. |
| 2013/0123797 A1 | 5/2013 | Livneh |
| 2013/0138145 A1* | 5/2013 | von Oepen ........ A61B 17/0057 606/213 |
| 2014/0257112 A1 | 9/2014 | Siegel |

* cited by examiner

SURGICAL INSTRUMENTS FOR TISSUE REMOVAL

TECHNICAL FIELD

The present disclosure generally relates to surgical instruments, and more particularly, to surgical instruments for removing tissue, such as, for example, uterine tissue.

BACKGROUND

A laparoscopic procedure is typically performed by passing surgical instruments down a cannula so that a distal working end of the surgical instrument can be positioned within the surgical site, while operated from a proximal manipulator of the surgical instrument. In certain surgical procedures, such as hysterectomies, fibroidectomies, myomectomies, and the like, laparoscopic morcellation is performed. In these procedures, for example, an endo knife may be used to remove a uterus, uterine fibroids (known as leiomyomas), and/or other tissue through a small abdominal incision.

Generally, removal of large amounts of tissue through abdominal incisions during laparoscopic surgeries may be achieved by feeding the tissue into a moving cutting tool, such as a morcellator, operating within the body cavity. For example, the endo knife may cut the uterus into long lengths of tissue, which are then morcellated and subsequently pulled out of the body cavity through the vaginal path. However, because these surgical instruments must be manually moved over the tissue during cutting, the procedure may be relatively time consuming and reliant on surgeon technique. Further, due to their proximity to other delicate structures in the abdomen, surgeons may have difficulty navigating the surrounding tissue. Thus, although morcellation and use of the endo knife are effective, they may be improved.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure, is a surgical instrument including a sleeve, a shaft slidably disposed within the sleeve and defining a longitudinal axis, and a plurality of legs coupled to the shaft and disposed about the longitudinal axis. Each leg has a blade attached to an end portion thereof. Each blade defines a cutting edge. The shaft is slidable relative to the sleeve between a collapsed configuration, wherein the legs are disposed within the sleeve, and an expanded configuration, wherein the legs extend distally and radially outwardly from the sleeve. In the expanded configuration, the cutting edge of each blade is disposed in a proximally-facing orientation.

In an aspect of the present disclosure, each blade is hook-shaped and extends radially inwardly from a free end of the corresponding leg.

In another aspect of the present disclosure, the legs are equally spaced about the longitudinal axis. Additionally, or alternatively, the legs are substantially equal in length.

In yet another aspect of the present disclosure, in the expanded configuration, each leg defines an arcuate configuration. The legs, more specifically, may cooperate to define a portion of a sphere in the expanded condition.

In still another aspect of the present disclosure, each blade further includes a pointed distal tip disposed in a radially-inwardly-facing orientation when the shaft is disposed in the expanded configuration.

Another surgical instrument for cutting tissue provided in accordance with aspects of the present disclosure includes a sleeve, a shaft slidably disposed within the sleeve and rotatable relative thereto, and a plurality of legs coupled to the shaft and disposed about a longitudinal axis of the shaft. Each leg defines a different length and has a blade attached to an end portion thereof. Each blade defines a cutting edge. The shaft is slidable relative to the sleeve between a collapsed configuration, wherein the legs are disposed within the sleeve, and an expanded configuration, wherein the legs extend distally and radially outwardly from the sleeve. In the expanded configuration, the shaft is rotatable relative to the sleeve to rotate the legs about the longitudinal axis, thereby rotating each blade through a circular cutting path. The circular cutting paths of the blades are concentrically arranged and defines different diameters. In the expanded configuration, the cutting edge of each blade is aligned on the corresponding circular cutting path.

In an aspect of the present disclosure, each leg has an inwardly-facing surface facing the longitudinal axis of the shaft, an outwardly-facing surface opposite the inwardly-facing surface, and side surfaces joining the inwardly-facing and outwardly-facing surfaces. In such aspects, each blade extends from one of the side surfaces of the corresponding leg. Further, each of the blades may extend from the one side surface of the corresponding leg in a similar direction.

In another aspect of the present disclosure, the legs are equally spaced about the longitudinal axis.

In still another aspect of the present disclosure, in the expanded configuration, each leg defines an arcuate configuration.

In yet another aspect of the present disclosure, in the expanded configuration, the legs cooperate to define a portion of a sphere.

In still yet another aspect of the present disclosure, a knob is disposed at a proximal end portion of the shaft. The knob is configured to facilitate rotation of the shaft relative to the sleeve.

A method of cutting tissue provided in accordance with aspects of the present disclosure includes positioning a surgical instrument, in a collapsed configuration, adjacent a target area of tissue. The surgical instrument includes a sleeve, a shaft slidably disposed within the sleeve, and a plurality of legs coupled to the shaft. Each leg has a blade attached to an end portion thereof. In the collapsed configuration, the legs are disposed within the sleeve.

The method further includes transitioning the legs from the collapsed configuration to an expanded configuration, wherein the legs extend distally and radially outwardly from the shaft and cooperate to define a portion of a sphere. The method additionally includes manipulating the surgical instrument such that the target area is at least partially disposed within the portion of the sphere, and actuating the surgical instrument such that each of the blades makes an elongated cut within the target area.

In an aspect of the present disclosure, actuating the surgical instrument includes moving the legs from the expanded configuration towards the collapsed configuration such that the blades are urged radially inwardly into the target area and proximally along the target area. In such aspects each blade may include a pointed distal tip configured to facilitate radially inward urging of the blade into the target area and/or a proximally-facing cutting edge configured to facilitate proximal movement of the blade along the target area.

In another aspect of the present disclosure, actuating the surgical instrument includes rotating the legs about the target area such that each blade makes an elongated cut along a circumference defined about the target area. In such aspects, each leg may define a different length such that each blade makes an elongated cut along a different circumference defined about the target area.

BRIEF DESCRIPTION OF THE DRAWINGS

The above and other aspects and features of the present disclosure will become more apparent in light of the following detailed description when taken in conjunction with the accompanying drawings, in which.

DETAILED DESCRIPTION

Surgical instruments for cutting tissue are provided, each generally including a shaft with a plurality of expandable legs advanceable through a sleeve, with each leg having a blade attached to a distal end portion thereof. In use, the surgical instrument, while in a collapsed configuration, is navigated into an internal surgical site and placed adjacent to a target area of tissue. A user may then manipulate the shaft to cause the legs to transition to an expanded configuration. The expanded legs are used to grasp tissue. In embodiments, the user may pull the shaft to collapse the legs and thereby cut tissue. Additionally, or alternatively, the user may rotate the shaft to correspondingly rotate the legs to cut tissue. These and other aspects and features of the present disclosure are described in detail below.

Figure 1:
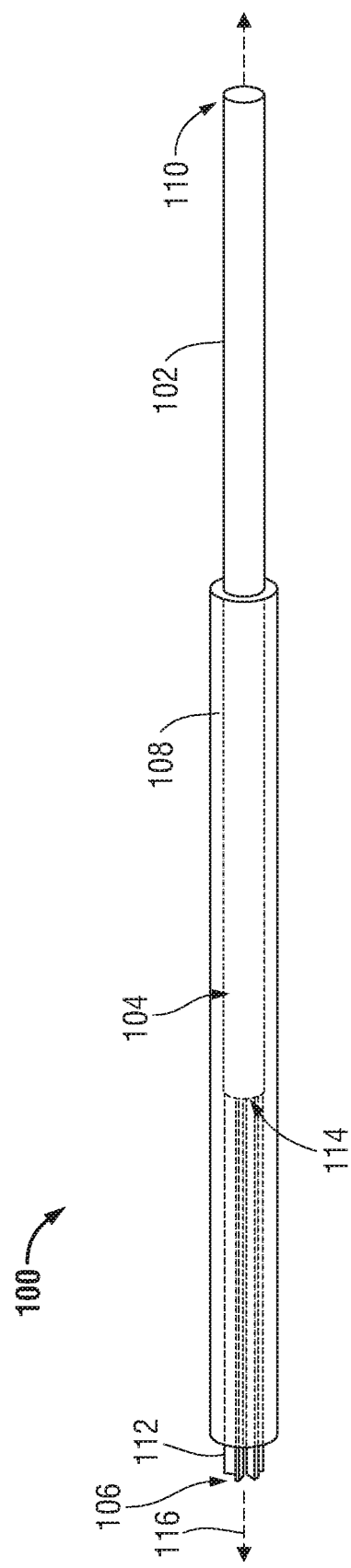
FIG. 1 is a perspective view of a surgical cutting instrument provided in accordance with the present disclosure, in a collapsed configuration.
Figure 2:
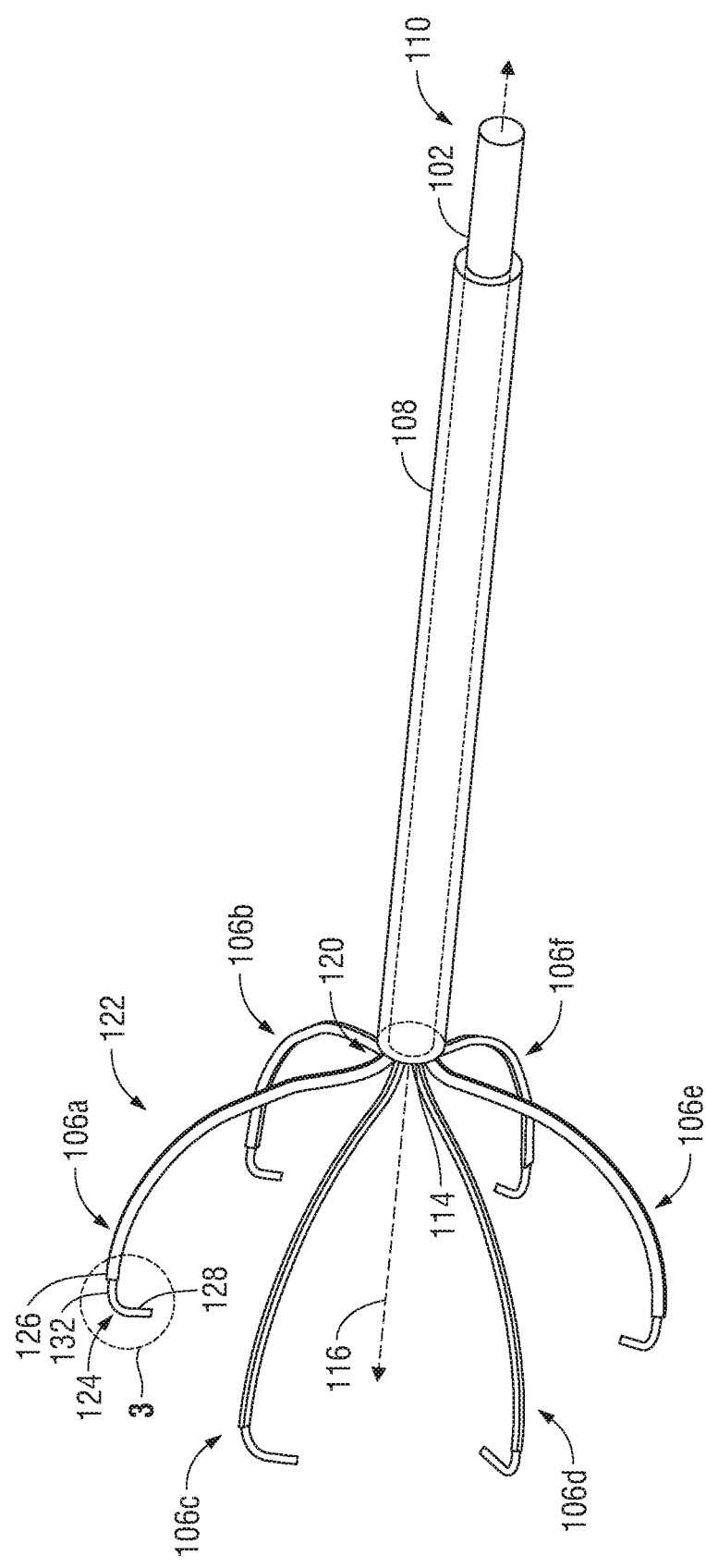
FIG. 2 is a perspective view of the surgical cutting instrument of FIG. 1 in an expanded configuration.

With reference to FIGS. 1 and 2, a surgical cutting instrument provided in accordance with the present disclosure is generally identified by reference numeral 100. Surgical instrument 100 includes a shaft 102 having a distal end portion 104 coupled to a plurality of legs 106a-106f (collectively, legs 106) configured to transition between a collapsed configuration (FIG. 1) and an expanded configuration (FIG. 2). In embodiments, to retain the plurality of legs 106a-106f in the collapsed configuration, the distal end portion 104 of the shaft 102 and the corresponding portions of the plurality of legs 106a-106f, are slidably disposed within a sleeve 108. The shaft 102 has a proximal end portion 110 configured to permit a user to advance the legs 106 through a distal opening 112 of the sleeve 108 or to retract the legs 106 back into the sleeve 108.

With continued reference to FIGS. 1 and 2, the shaft 102 is configured to be relatively stiff to inhibit bending. In embodiments, the shaft 102 may be configured to maintain its stiffness throughout the entirety of a surgical procedure, or to stiffen upon application of heat, electrical energy, or in response to a change of temperature (e.g., from room temperature to body temperature). For example, the shaft 102 may be made of materials, such as stainless steel or a polymer, Nitinol, and the like. The shaft 102 may have a length suitable to extend through an access opening or port (not shown) and into an internal surgical site. Further, although depicted as having a relatively uniform outer diameter along its length, the shaft 102 may taper to a narrower outer diameter toward the distal end portion 104 or the proximal end portion 110 thereof, or may define a stepped configuration having multiple sections of similar, different, or tapering diameter.

The legs 106 extend from the shaft 102 and are substantially equally spaced around a longitudinal axis 116 of the shaft 102, although legs 106 may alternatively be arranged in any other suitable configuration. Although six (6) legs 106a-106f are shown, fewer or more may be included. For example, five (5) legs may be included. In embodiments, three (3) or more legs 106 may be included. The legs 106a-106f are substantially equal in length, although other configurations are also contemplated. As detailed below, legs 106a1-6f cooperate to cut tissue during use.

With particular reference to FIG. 2, the legs 106 may be formed from stainless steel to maintain their original shape regardless of whether they are in the collapsed or expanded configuration. In another embodiment, the legs 106 are made of a flexible material having a spring constant that permits temporary deforming, for example, into the collapsed configuration. Each leg 106a-106f has an attachment portion 120 and a body portion 122 including a blade 124. For simplicity, the details of the parts of the legs 106 will be described with reference to a single one of the legs 106a, however it will be appreciated each leg 106b-106f includes the same parts as leg 106a.

The attachment portion 120 of leg 106a extends distally from the distal end 114 of the shaft 102 at an angle relative to the longitudinal axis 116. For example, the angle may be in a range of about 30 to about 90 degrees, about 45 to about 90 degrees, or about 60 to about 80 degrees. To couple the leg 106a to the shaft 102, the attachment portion 120 of the leg 106a may be inserted into a corresponding notch or groove (not shown) at the distal end 114 of the shaft 102 containing adhesive therein, via press-fitting, or other suitable engagement. In other embodiments, the attachment portion 120 is integrally formed as part of the shaft 102. For example, the distal end portion 104 of the shaft 102 may be formed around the attachment portion 120 of the leg 106a.

The body portion 122 of leg 106a extends from attachment portion 120 and may define an arcuate configuration along at least a portion of the length thereof, although other configurations are also contemplated. More specifically, body portion 122 may define a curvature such that, when the legs 106a-106f are disposed in the expanded condition, the body portions 122 of the legs 106 together define a portion of a sphere with the distal ends of the legs 106 disposed about the perimeter of a circle having a diameter. Further, no matter the particular diameter when in the expanded condition, the curvature of the body portions 122 is selected so when the legs 106a-106f are disposed in the collapsed configuration, an outer diameter of the legs 106 is smaller than an inner diameter of the sleeve 108, enabling the legs 106 to fit within the sleeve 108. In another embodiment, the body portions 122 are not curved, but instead extend from the respective attachment portions 120 in a substantially straight manner to define a cone with the distal ends of the legs 106 disposed about the perimeter of a circle having a diameter at the base of the cone.

A blade 124 made of surgical steel, or other suitable material, extends from the body portion 122 of the leg 106a to facilitate tissue cutting, as detailed below. In embodiments, the blade 124 extends from a terminal end 126 of the body portion 122 of the leg 106a along a similar arc or line therewith. Alternatively, the blade 124 may extend from the terminal end 126 of the body portion 122 at an angle relative to the arc or line the terminal end 126 of the body portion 122 follows. In either configuration, blade 124 includes a bend of appropriate angle (depending upon the configuration of blade 124) such that at least a free end portion of the blade 124 extends in a radially inward direction, thus defining a hook-shaped configuration of blade 124. The blade 124 may have any one of numerous particular blade configurations, as detailed below.

Figure 3:
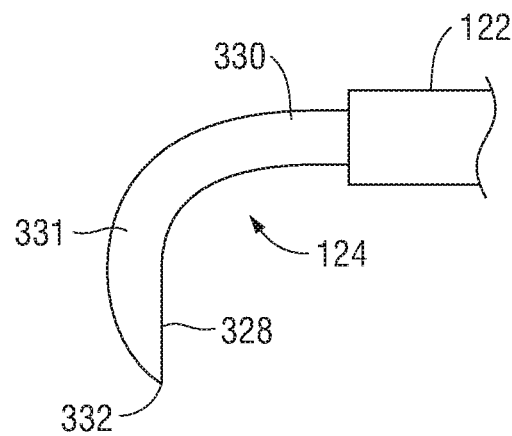
FIG. 3 is an enlarged, perspective view of a distal portion of a leg of the surgical cutting instrument of FIG. 1, indicated by the area of detail indicated as "3" in FIG. 1.

For example, according to embodiments, as depicted in FIG. 3, the blade 124 may include a base portion 330 and a tip portion 331 angled relative to base portion 330. Tip portion 331, more specifically, is talon-shaped and angled relative to base portion 330 such that tip portion 331 extends in a radially inward direction and defines a sharpened proximally-facing edge 328. Tip portion 331 further includes a sharp distal tip 332 facing radially-inwardly.

Figure 4:
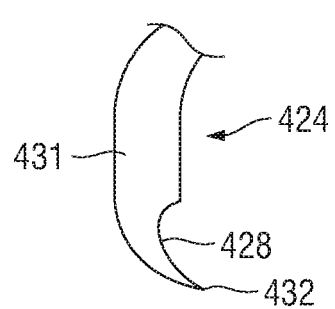
FIG. 4 is an enlarged, perspective view of a distal portion of another leg configured for use with the surgical cutting instrument of FIG. 1.

In other embodiments, as depicted in FIG. 4, the tip portion 431 of the blade 424 has a clip point shape and is angled relative to the base portion (not shown) such that tip portion 431 extends in a radially inward direction and defines a concave, sharpened proximally-facing edge 428 and a sharp distal tip 432 facing radially-inwardly.

Figure 5:
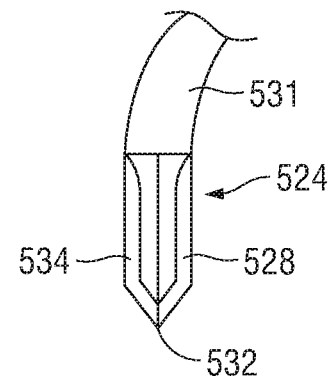
FIG. 5 is an enlarged, perspective view of a distal portion of another leg configured for use with the surgical cutting instrument of FIG. 1.

In still other embodiments, as illustrated in FIG. 5, the tip portion 531 of the blade 524 defines a dagger shape and is angled such that opposed sharp edges 528, 534 are proximally and distally-facing, respectively, and such that sharp distal tip 432 faces radially-inwardly.

The use of surgical cutting instrument 100 (FIG. 1) to cut tissue is detailed below.

Figure 6:
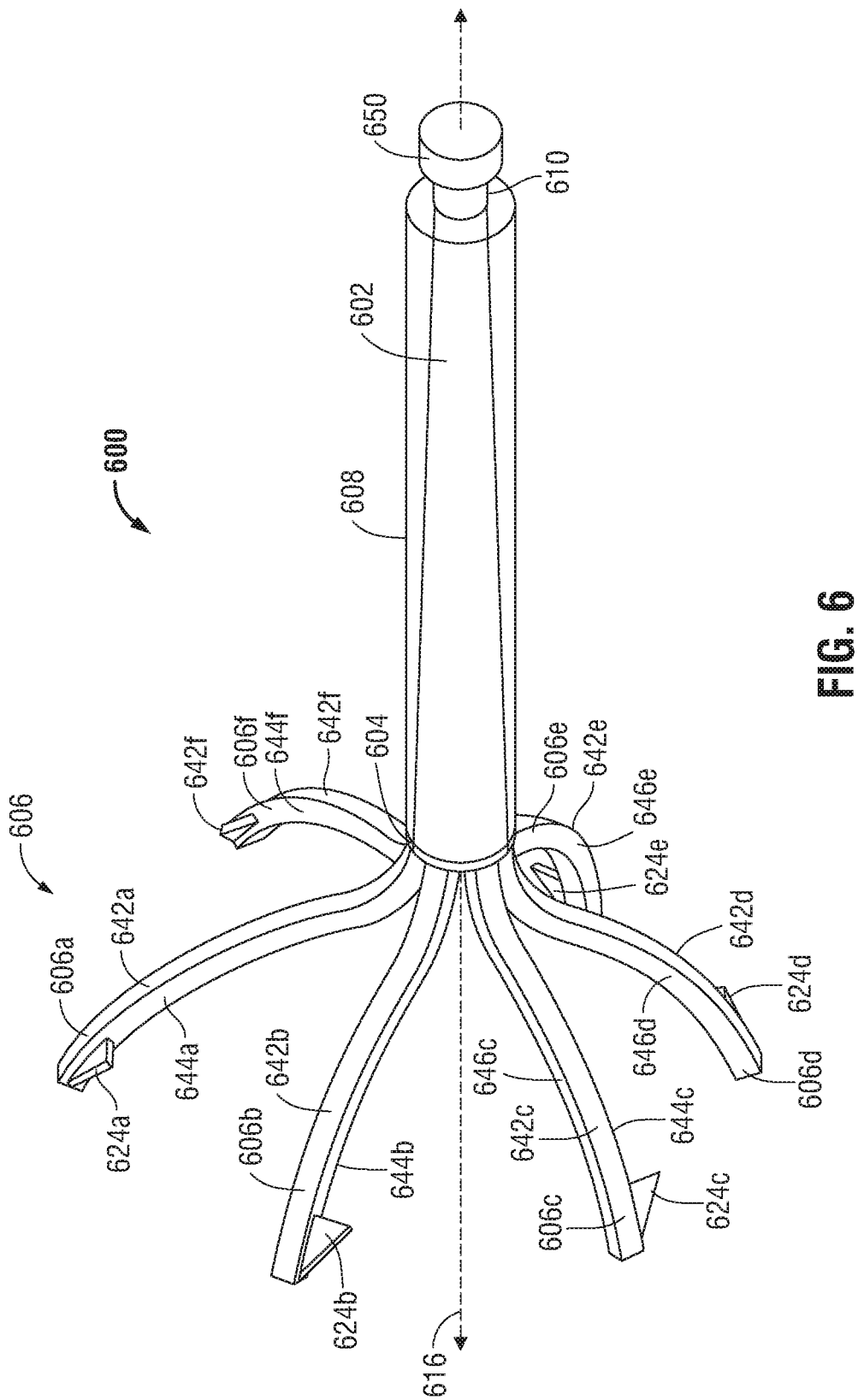
FIG. 6 is a perspective view of another surgical cutting instrument provided in accordance with the present disclosure, in an expanded configuration.
Figure 7:
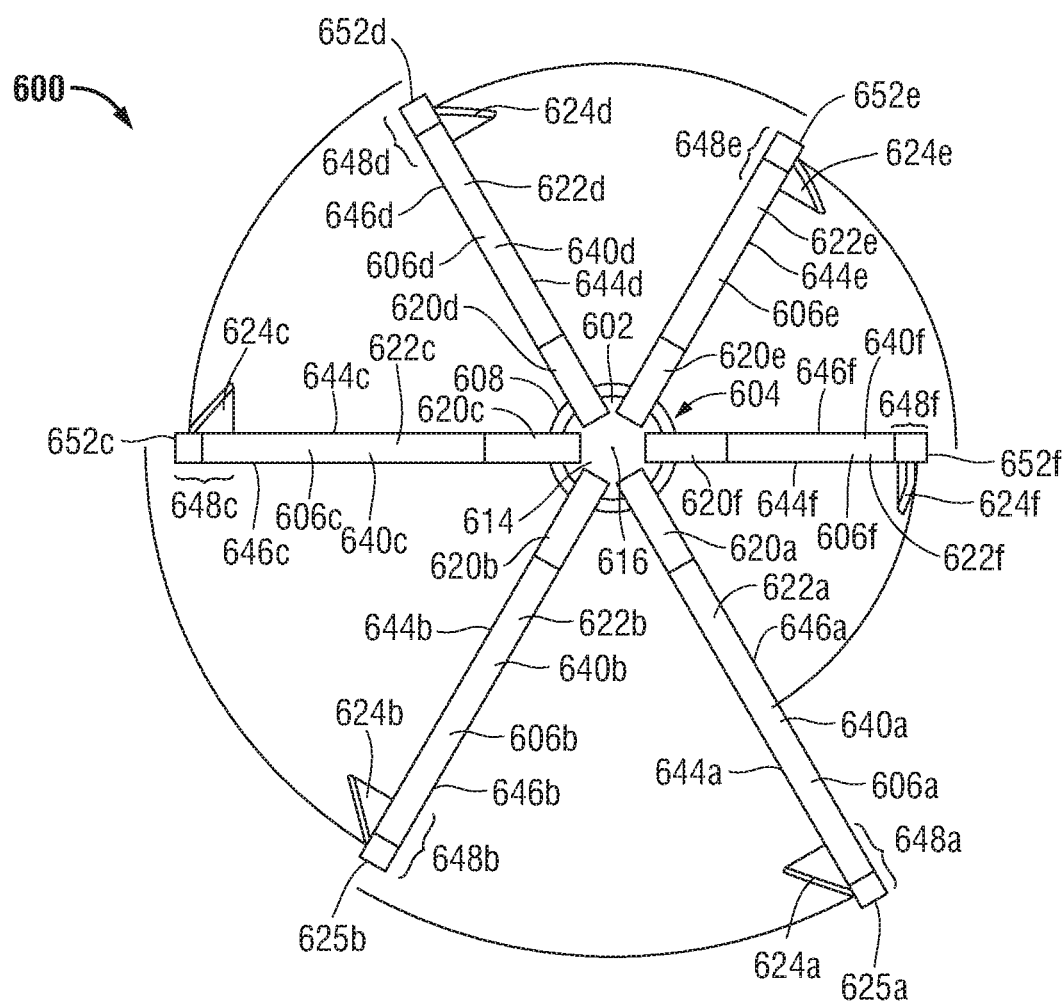
FIG. 7 is a distal end view of the surgical cutting instrument of FIG. 6, in the expanded configuration.
Figure 8:
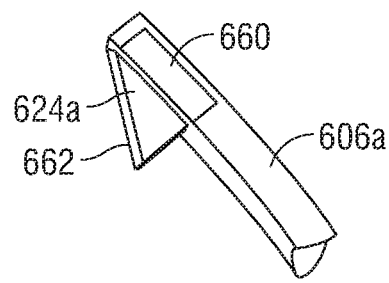
FIG. 8 is an enlarged, perspective view of a distal end portion of a leg of the surgical cutting instrument of FIG. 6.

Turning now to FIGS. 6-8, another surgical cutting instrument provided in accordance with the present disclosure is generally identified by reference numeral 600. Here, the surgical cutting instrument 600 includes a shaft 602 having a plurality of legs 606a-606f (collectively, legs 606) coupled to a distal end portion 604 of shaft 602, with blades 624a-624f extending transversely from the legs 606. The shaft 602 and, thus, the legs 606, are slidably disposed within a sleeve 608. Additionally, the surgical cutting instrument 600 has a knob 650 coupled to a proximal end portion 610 of the shaft 602. The knob 650 may be configured to be manipulated by the user in a rotating and/or push/pull fashion to thereby rotate and/or advance/retract the legs 606 through the sleeve 608. Surgical cutting instrument 100 (FIG. 1) may likewise include a knob (not shown) to facilitate push/pull manipulation. Other suitable manipulation components, e.g., levers, paddles, pull-rings, etc., are also contemplated.

Similar to the shaft 102 described above with respect to FIG. 1, the shaft 602 of surgical cutting instrument 600 has a distal end portion 614 (FIG. 7), which may include channels or grooves (not shown) for the attachment of corresponding legs 606. The shaft 602 is generally stiff to thereby maintain its shape at all times during a surgical procedure, and in this regard, may be made of a material such as stainless steel or a suitably stiff biocompatible polymer, although the shaft 602 may alternatively be selectively stiffening, similarly as detailed above with respect to shaft 102 (FIG. 1). Although depicted as having an increasing outer diameter along its length, the shaft 602 may taper to a narrower outer diameter toward the proximal end portion 610, may be relatively uniform in diameter, or may define a stepped configuration.

As depicted in the figures, six (6) legs 606 are substantially equally spaced around a longitudinal axis 616 of the shaft 602. As with surgical cutting instrument 100, fewer or more legs 606 may be included as part of surgical cutting instrument 600. The legs 606a-606f each have a radially-inward surface 640a-640f facing the longitudinal axis 616 of the shaft 602, a radially-outward surface 642a-642f opposite the interior surface 640a-640f and facing radially-outwardly relative to the longitudinal axis 616, and a pair of side surfaces 644a-644f, 646a-646f joining the radially-inward surfaces 640a-640f and the radially-outward surfaces 642a-642f.

As best shown in FIG. 7, each leg 606a-606f is configured such that each is successively shorter in length as compared to a neighboring one of the legs 606a-606f, when viewed in a clockwise direction (from the orientation illustrated in FIG. 7), to define concentric, non-overlapping circular cutting paths 648a-648f. As a result, when rotated about the longitudinal axis 616, distal ends 652a-652f of the legs 606a-606f each travel along perimeters of these circular cutting paths 648a-648f, which have different diameters.

Although each of the legs 606a-606f is different in length, each is otherwise similar. In particular, each of the leg 606a-606f has an attachment end portion 620a-620f that extends from the distal end 614 of the shaft 602 and curves radially outwardly in substantially the same manner relative to the longitudinal axis 616. Alternatively, each attachment end portion 620a-620f is substantially straight.

Each of the body portions 622a-622f of legs 606a-606f extends from the corresponding attachment end portions 620a-620f in substantially similar configurations, except, as noted above, for their lengths. In embodiments, the body portions 622a-622f define arcuate configurations in a manner such that when the legs 606 are disposed in the expanded configuration, the body portions 622a-622f together define a portion of a sphere (and may be similarly or differently angled as attachment portions 120 of legs 106a-106f of surgical cutting instrument 100 (FIGS. 1-2)). In other embodiments, the body portions 622a-622f are substantially straight to define a cone-shaped configuration.

The blades 624a-624f are disposed at distal end portions of corresponding legs 606a-606f. More particularly, each blade 624a-624f is aligned on the circular cutting path 648a-648f of the corresponding leg 606a-606f. Blades 624a-624f are disposed on side surfaces 644a-644f of the legs 606a-606f and extend therefrom towards a neighboring leg 606a-606f such that blades 624a-624f are disposed on the portion of the sphere defined by legs 606. Legs 606a-606f define relative lengths such that each blade 624a-624f is able to rest over a distal end 652a-652f of the shorter neighboring leg 606a-606f in the collapsed configuration of legs 606a-606f. Alternatively, slits or grooves (not shown) may be formed in some or all of the legs 606a-60a to receive the blade 624a-624f of a neighboring leg 606a-606f.

The blades 624a-624f are substantially identical in shape. With reference to FIG. 8, the blade 624a may have an attachment side portion 660 that may be inserted into and engaged with or integrally formed as part of the leg 606a. For simplicity, the details of the parts of the blade 624 will be described with reference to a single one of the blades 624a, however it will be appreciated each blade 624a-624f includes the same parts as blade 624a. The exposed portion of blade 624a defines a substantially right-triangular configuration and includes an angled cutting edge 662 along a hypotenuse side of the blade 624a so as to face in a distally and clockwise direction (from the orientation illustrated in FIGS. 7 and 8). In other embodiments, the cutting edge 662 further extends along the side of exposed portion of blade 624a that is adjacent the hypotenuse side. In still other embodiments, the blade 624a is substantially rectangular and one or more of the edges making up the blade 624a are sharpened.

Returning to FIGS. 6 and 7, the knob 650 is coupled to the proximal end portion 610 of the shaft 602. For example, the knob 650 may be welded or otherwise adhered to the proximal end portion 610 of the shaft 602, or may be integrally formed as a portion of the shaft 602. In either case, the outer surface of the knob 650 may be textured to improve grip to allow a user to more easily grasp the knob 650 for twisting to cause rotation of the legs 606 or for pulling to retract or advance the legs 606 into and out of the sleeve 608.

Referring generally to FIGS. 1-8, to use one of the surgical cutting instruments described above (e.g., surgical cutting instrument 100 or surgical cutting instrument 600 to cut tissue), the selected surgical cutting instrument 100, 600, while in a collapsed configuration, is positioned adjacent a target area of tissue. More specifically, the surgical cutting instrument 100, 600 may be advanced through a cannula previously placed in a patient's body at a particular location. Once the surgical cutting instrument 100, 600 is suitably positioned, the user manipulates, e.g., pushes, the proximal end portion 110 of the shaft 102 (for surgical cutting instrument 100) or the knob 650 (for surgical cutting instrument 100) to advance the shaft 102, 602 distally through the sleeve 108, 608 and towards the tissue to thereby advance the legs 106, 606 out of the distal opening 112, 604 of the sleeve 108, 608. As a result, the legs 106, 606 are transitioned from the collapsed configuration within sleeve 108, 608, to the expanded configuration, wherein legs 106, 606 extend distally from sleeve 108, 608 and radially outwardly relative thereto. Depending on various considerations, such as the size of the tissue to be cut, the legs 106, 606 may be expanded only to a partially expanded configuration, or may be extended to a fully expanded configuration. If needed, the proximal end portion 110 of the shaft 102 (for surgical cutting instrument 100) or the knob 650 (for surgical cutting instrument 600) may be further manipulated to reposition the partially or fully expanded legs 106, 606 to a location within the target area to surround target tissue.

With reference to FIGS. 1-2, to engage and cut tissue using surgical cutting instrument 100, legs 106 are positioned such that tissue to be engaged and cut is disposed within the portion of the sphere defined by legs 106. With surgical cutting instrument 100 positioned in this manner, the user may further manipulate the proximal end portion 110 of the shaft 102 to pull the shaft 102 proximally through the sleeve 108 and away from the tissue, thereby moving the legs 106 towards the collapsed configuration, which results in the blades 124 moving radially inwardly to initially grasp and, in embodiments, cut radially inwardly into the target tissue disposed within the sphere defined by legs 106 (using sharp distal tips 332 of blades 124 (FIG. 3)). During this and further movement of the legs 106 towards the collapsed configuration, legs 106 are pulled proximally relative to tissue such that the target tissue is cut along its length (using sharpened proximally-facing edge 328 (FIG. 3)). Thus, by the combined radially-inward and proximal movement of blades 124, tissue is cut into slices to facilitate removal from an internal surgical site.

Referring to FIGS. 6-7, when using surgical cutting instrument 600, the knob 650 may initially be pulled proximally to grasp tissue disposed within the sphere defined by legs 606 and, in embodiments, compress legs 606 about such tissue. Knob 650 may then be rotated in a clockwise or counterclockwise direction (depending on the orientation of the blades 624) to cause the legs 606 to correspondingly rotate and thereby cut through the target tissue using blades 624. More specifically, due to legs 606 defining different lengths, a plurality of circular strips of tissue are cut along the length of the target tissue to facilitate removal from an internal surgical site.

With respect to both surgical cutting instrument 100 (FIGS. 1-2) and surgical cutting instrument 600 (FIGS. 7-8), the above-detailed procedure of advancing, positioning, and pulling/rotating proximal end portion 110 of the shaft 102 (for surgical cutting instrument 100) or the knob 650 (for surgical cutting instrument 600) is repeated as necessary, until the target tissue is cut into the desired size, e.g., sufficiently small slices or strips to enable removal through a minimally-invasive opening (surgically created or naturally occurring).

It is also envisioned that surgical cutting instrument 100 (FIGS. 1-2) and surgical cutting instrument 600 (FIGS. 7-8) be configured for use within a specimen retrieval bag (not shown) to protect surrounding tissue during cutting of the tissue specimen into slices or strips to enable removal. In such configurations, the open end of the specimen retrieval bag (not shown) may be cinched or otherwise closed about the sleeve 108, 608 of the surgical cutting instrument 100, 600, respectively, to enclose the distal end of the instrument 100, 600 (including legs 106, 606) and the tissue therein.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A surgical instrument for cutting tissue comprising:
   a sleeve;
   a shaft slidably disposed within the sleeve, the shaft defining a longitudinal axis; and a plurality of legs coupled to the shaft and disposed about the longitudinal axis, each leg of the plurality of legs having a blade attached to an end portion thereof, each blade defining a cutting edge, wherein the shaft is slidable relative to the sleeve between a collapsed configuration, wherein the plurality of legs are disposed within the sleeve, and an expanded configuration, wherein the plurality of legs extend distally and radially outwardly from the sleeve, wherein, in the expanded configuration, the cutting edge of each blade is disposed in a proximally-facing orientation, and wherein each blade includes a pointed distal tip disposed in a radially inwardly facing orientation in the expanded configuration at a position distal of a distal end of the sleeve.

2. The surgical instrument of claim 1, wherein each blade is hook-shaped and extends radially inwardly from a free end of the corresponding leg of the plurality of legs.

3. The surgical instrument of claim 1, wherein the plurality of legs are equally spaced about the longitudinal axis.

4. The surgical instrument of claim 1, wherein the plurality of legs are substantially equal in length.

5. The surgical instrument of claim 1, wherein, in the expanded configuration, each leg of the plurality of legs defines an arcuate configuration.

6. The surgical instrument of claim 5, wherein, in the expanded configuration, the plurality of legs cooperate to define a portion of a sphere.

* * * * *